(12) United States Patent
Kim et al.

(10) Patent No.: US 11,707,202 B2
(45) Date of Patent: Jul. 25, 2023

(54) APPARATUS FOR GENERATING FIELD-FREE REGION, APPARATUS AND METHOD FOR NANO MAGNETIC PARTICLE IMAGE

(71) Applicant: Electronics and Telecommunications Research Institute, Daejeon (KR)

(72) Inventors: Jin-Sun Kim, Daejeon (KR); Jae-Chan Jong, Daejeon (KR); Hyo-Bong Hong, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 17/466,898

(22) Filed: Sep. 3, 2021

(65) Prior Publication Data
US 2022/0087564 A1   Mar. 24, 2022

(30) Foreign Application Priority Data

Sep. 24, 2020   (KR) .................. 10-2020-0123972
Apr. 23, 2021   (KR) .................. 10-2021-0053209

(51) Int. Cl.
| | | |
|---|---|---|
| *A61B 5/0515* | (2021.01) | |
| *A61K 49/18* | (2006.01) | |
| *G01R 33/48* | (2006.01) | |
| *H01F 1/00* | (2006.01) | |
| *B82Y 25/00* | (2011.01) | |

(52) U.S. Cl.
CPC ........ *A61B 5/0515* (2013.01); *A61K 49/1818* (2013.01); *G01R 33/481* (2013.01); *H01F 1/0045* (2013.01); *B82Y 25/00* (2013.01)

(58) Field of Classification Search
CPC ... A61B 5/0515; G01R 33/481; H01F 1/0045; B82Y 25/00
See application file for complete search history.

(56) References Cited

U.S. PATENT DOCUMENTS

| | | | |
|---|---|---|---|
| 5,621,324 A * | 4/1997 | Ota ..................... | G01R 33/383 324/319 |
| 8,610,436 B2 * | 12/2013 | Besio .................. | G01R 33/383 324/319 |
| 9,041,230 B2 * | 5/2015 | Arnold ................. | H02K 35/04 290/1 R |
| 10,359,481 B2 | 7/2019 | Wald et al. | |
| 10,667,716 B2 | 6/2020 | Goodwill et al. | |
| (Continued) | | | |

FOREIGN PATENT DOCUMENTS

KR   1020150023024 A   3/2015

*Primary Examiner* — Dixomara Vargas
(74) *Attorney, Agent, or Firm* — William Park & Associates Ltd.

(57) ABSTRACT

Disclosed herein is an apparatus for imaging nano magnetic particles using a 3D array of small magnets. A field-free region generation apparatus includes a hexahedral housing having an opening formed in the first surface thereof such that a measurement head is inserted into a spacing area, a pair of rectangular-shaped magnets installed respectively on two surfaces facing each other, among four surfaces perpendicular to the first surface of the housing, and a pair of magnet arrays installed respectively on the first surface of the housing and on another surface facing the first surface, each of the magnet arrays including multiple small magnets arranged along the edge of the opening.

18 Claims, 17 Drawing Sheets

(56) References Cited

U.S. PATENT DOCUMENTS

| | | | | |
|---|---|---|---|---|
| 2009/0261826 | A1* | 10/2009 | Pines | G01R 33/445 |
| | | | | 324/309 |
| 2012/0265050 | A1* | 10/2012 | Wang | A61B 6/485 |
| | | | | 600/407 |
| 2015/0177343 | A1* | 6/2015 | Wald | G01R 33/28 |
| | | | | 324/309 |
| 2015/0276902 | A1* | 10/2015 | Weaver | G01R 33/4808 |
| | | | | 324/309 |
| 2017/0067972 | A1* | 3/2017 | Diamond | G01R 33/1276 |
| 2018/0064365 | A1* | 3/2018 | Srinivasan | A61G 11/00 |
| 2018/0074144 | A1 | 3/2018 | Dezorayev et al. | |
| 2018/0231629 | A1* | 8/2018 | Top | A61B 5/0515 |
| 2018/0335487 | A1* | 11/2018 | To | G01R 33/1276 |
| 2020/0132786 | A1* | 4/2020 | Takano | G01R 33/0094 |
| 2021/0208215 | A1* | 7/2021 | Takano | G01R 33/098 |

* cited by examiner

LOCATION OF FFL

APPARATUS FOR GENERATING FIELD-FREE REGION, APPARATUS AND METHOD FOR NANO MAGNETIC PARTICLE IMAGE

CROSS REFERENCE TO RELATED APPLICATIONS

This application claims the benefit of Korean Patent Application No. 10-2020-0123972, filed Sep. 24, 2020, and No. 10-2021-0053209, filed Apr. 23, 2021, which are hereby incorporated by reference in their entireties into this application.

BACKGROUND OF THE INVENTION

1. Technical Field

The disclosed embodiment relates generally to technology for imaging a specific object included in a sample, and more particularly to technology for imaging the spatial distribution of Nano Magnetic Particle (NMP) materials.

2. Description of the Related Art

Magnetic Particle Imaging (MPI) using superparamagnetic iron oxide nano particles (SPIOs) is technology for medical imaging equipment expected to replace Positron Emission Tomography (PET), and is the next-generation medical imaging technique, and a lot of research and development thereon has been underway since the principle thereof was published in 2005.

In order to realize an MPI device that is scalable to 3D space, it is necessary to generate a Field-Free Point (FFP) or a Field-Free Line (FFL), which is a field-free region in which the strength of a magnetic field is almost zero at a point, on a line, or in a plane in the space. Here, the steeper the gradient of the magnetic field in the FFP or FFL, the better the resolution. Therefore, generating such a region in the space is core technology in MPI.

Here, methods that have been proposed to date may be divided into two methods, which are a method of using an electromagnet and a method of using a permanent magnet, like all other methods for generating an electromagnetic field.

Here, the method of using an electromagnet may control the location at which an electromagnetic field is to be generated using the strength of current and the location of a coil. However, electromagnet-based MPI equipment that has been produced for commercial use or research has a disadvantage in that, although it consumes tens to hundreds kW of power, measurement can be performed only on a sample having a very small size, such as an experimental mouse.

In contrast, the method of using a permanent magnet has advantages in that it consumes little power and the size of equipment can be reduced, but requires the use of a large magnet in order to generate an FFL or FFP. Such a large magnet is difficult to produce, and the strength of magnetic force on the surfaces thereof is not uniform. Further, there is a risk of severe safety-related accidents due to the strong magnetic force, which may result in accidents upon practical implementation.

SUMMARY OF THE INVENTION

An object of an embodiment is to use a rectangular-shaped magnet having a medium size and an array of small magnets, rather than a large magnet, in order to realize generation of a field-free region for MPI using a permanent magnet, thereby overcoming the disadvantages with a large magnet.

An apparatus for generating a field-free region according to an embodiment may include a hexahedral housing in which an opening is formed in a first surface thereof such that a measurement head is inserted into a spacing area, a pair of rectangular-shaped magnets that are installed respectively on two surfaces facing each other, among four surfaces perpendicular to the first surface of the housing, and a pair of magnet arrays that are installed respectively on the first surface of the housing and on another surface facing the first surface, each of the magnet arrays including multiple small magnets arranged along the edge of the opening.

Here, the multiple small magnets may be arranged in a circular shape along the edge of the opening.

Here, the field-free region may be a Field-Free Point (FFP) or a Field-Free Line (FFL).

The apparatus for generating a field-free region according to an embodiment may further include a first driving unit for linearly moving or rotating the pair of rectangular-shaped magnets.

An apparatus for imaging nano magnetic particles according to an embodiment may include a measurement head in which a through hole for accommodating a sample including the nano magnetic particles is formed and in which an excitation coil and a detection coil are installed, a field-free region generation unit for forming a field-free region, in which there is a weak magnetic field or no magnetic field, in a spacing area between identical magnetic poles that face each other, and a control unit for applying a signal to the excitation coil when the measurement head is placed within the spacing area of the field-free region generation unit, controlling the field-free region so as to move in the sample, and imaging the 3D positional distribution of the nano magnetic particles included in the sample based on a detection signal output from the detection coil. The field-free region generation unit may include a pair of rectangular-shaped magnets and a pair of magnet arrays, in each of which multiple small magnets are arranged.

Here, the field-free region generation unit may include a hexahedral housing in which an opening is formed in a first surface thereof such that the measurement head is inserted into the spacing area, the pair of rectangular-shaped magnets that are installed respectively on two surfaces facing each other, among four surfaces perpendicular to the first surface of the housing, and the pair of magnet arrays that are installed respectively on the first surface of the housing and on another surface facing the first surface, each of the magnet arrays including the multiple small magnets arranged along the edge of the opening.

Here, the multiple small magnets may be arranged in a circular shape along the edge of the opening.

Here, the field-free region may be a Field-Free Point (FFP) or a Field-Free Line (FFL).

Here, the control unit may be configured to generate a 2D image, which is 2D positional distribution of nano magnetic particles included in a cross section of the sample, based on the detection signal and to generate a 3D image by synthesizing multiple 2D images corresponding to multiple cross sections that are parallel to each other.

The apparatus for imaging nano magnetic particles according to an embodiment may further include a first driving unit for linearly moving or rotating the pair of rectangular-shaped magnets.

Here, the control unit may be configured to repeatedly perform linear movement of the pair of rectangular-shaped magnets in one direction and rotation thereof so as to form a predetermined angle with the one direction by controlling the first driving unit; and to generate a sinogram using a signal output from the detection signal according to movement of the field-free region and generate the 2D image by performing inverse radon transform on the generated sinogram.

The apparatus for imaging nano magnetic particles according to an embodiment may further include a second driving unit for moving the measurement head to the spacing area via the opening in the field-free region generation unit.

Here, the control unit may repeat generation of the 2D image while moving the measurement head by a predetermined unit length in a direction perpendicular to the cross section of the sample.

A method for imaging nano magnetic particles according to an embodiment may include applying a signal to an excitation coil installed in a measurement head that accommodates a sample including the nano magnetic particles and moving a field-free region, in which there is a weak magnetic field or no magnetic field and which is generated in a spacing area between identical magnetic poles facing each other, in a sample and imaging 3D positional distribution of the nano magnetic particles included in the sample based on a detection signal output from a detection coil of the measurement head. The field-free region may be generated by a pair of rectangular-shaped magnets and a pair of magnet arrays, in each of which multiple small magnets are arranged.

Here, the pair of rectangular-shaped magnets may be configured such that the rectangular-shaped magnets are installed respectively on two surfaces facing each other, among four surfaces perpendicular to a first surface of a hexahedral housing, in the first surface of which an opening is formed such that the measurement head is inserted into the spacing area, and the pair of magnet arrays may be configured such that the magnet arrays are located respectively on the first surface of the housing and on another surface facing the first surface and such that the multiple small magnets are arranged along the edge of the opening.

Here, the multiple small magnets may be arranged in a circular shape along the edge of the opening.

Here, the field-free region may be a Field-Free Point (FFP) or a Field-Free Line (FFL).

Here, imaging the 3D positional distribution of the nano magnetic particles may include generating a 2D image, which is 2D positional distribution of nano magnetic particles included in a cross section of the sample, based on the detection signal and generating a 3D image by synthesizing multiple 2D images corresponding to multiple cross sections that are parallel to each other.

Here, generating the 2D image may be configured such that, while the pair of rectangular-shaped magnets is linearly moved in one direction or is rotated so as to form a predetermined angle with the one direction, a sinogram is generated using a signal output from the detection signal according to movement of the field-free region, and the 2D image is generated by performing inverse radon transform on the generated sinogram.

Here, generating the 2D image may be repeated while moving the measurement head by a predetermined unit length in a direction perpendicular to the cross section of the sample.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF THE PREFERRED EMBODIMENTS

Figure 1:
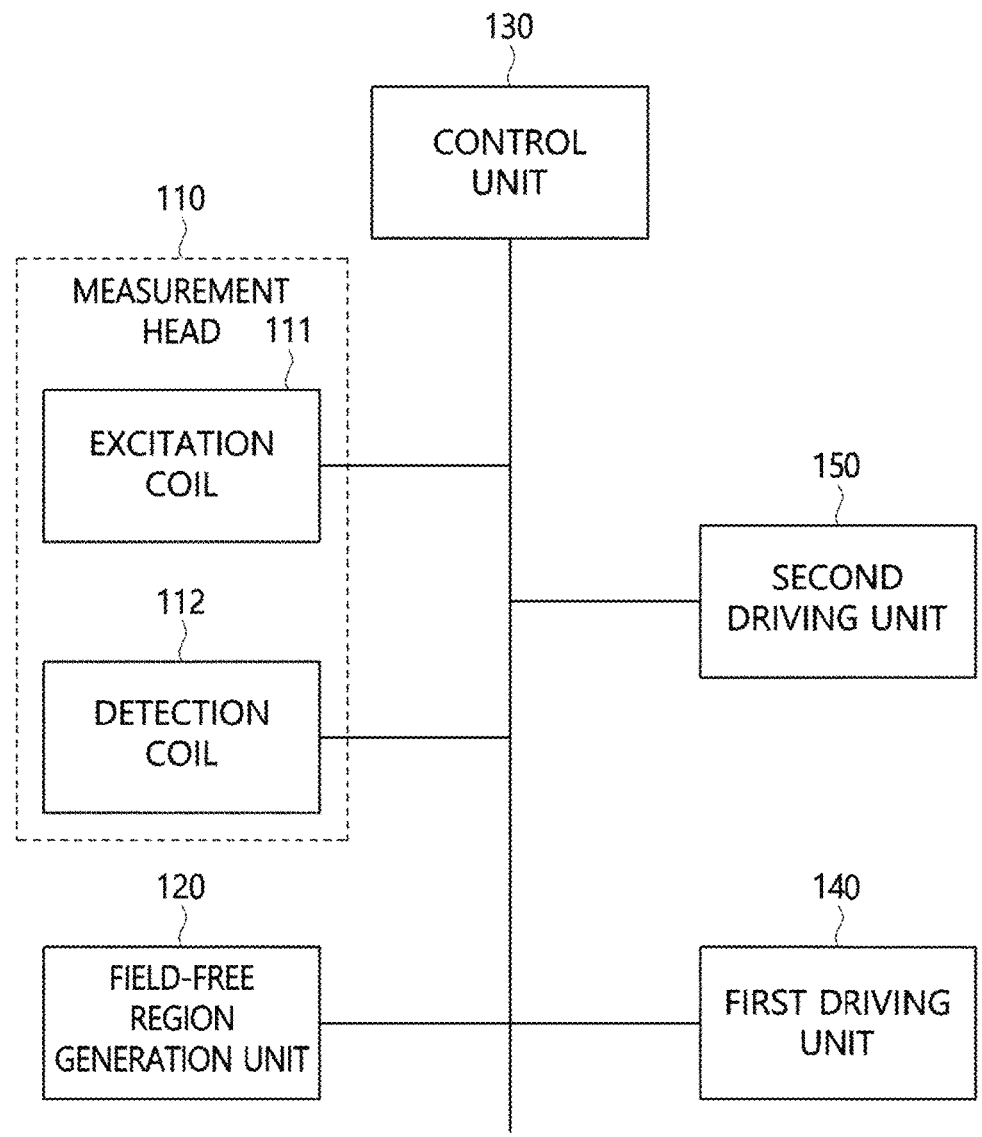
FIG. 1 is a schematic block diagram of an apparatus for imaging nano magnetic particles according to an embodiment.

The advantages and features of the present invention and methods of achieving the same will be apparent from the exemplary embodiments to be described below in more detail with reference to the accompanying drawings. However, it should be noted that the present invention is not limited to the following exemplary embodiments, and may be implemented in various forms. Accordingly, the exemplary embodiments are provided only to disclose the present invention and to let those skilled in the art know the category of the present invention, and the present invention is to be defined based only on the claims. The same reference numerals or the same reference designators denote the same elements throughout the specification.

It will be understood that, although the terms "first," "second," etc. may be used herein to describe various elements, these elements are not intended to be limited by these terms. These terms are only used to distinguish one element from another element. For example, a first element discussed below could be referred to as a second element without departing from the technical spirit of the present invention.

The terms used herein are for the purpose of describing particular embodiments only, and are not intended to limit the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless differently defined, all terms used herein, including technical or scientific terms, have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitively defined in the present specification.

Hereinafter, an apparatus for generating a field-free region and an apparatus and method for imaging nano magnetic particles according to an embodiment will be described in detail with reference to FIGS. 1 to 31.

Figure 2:
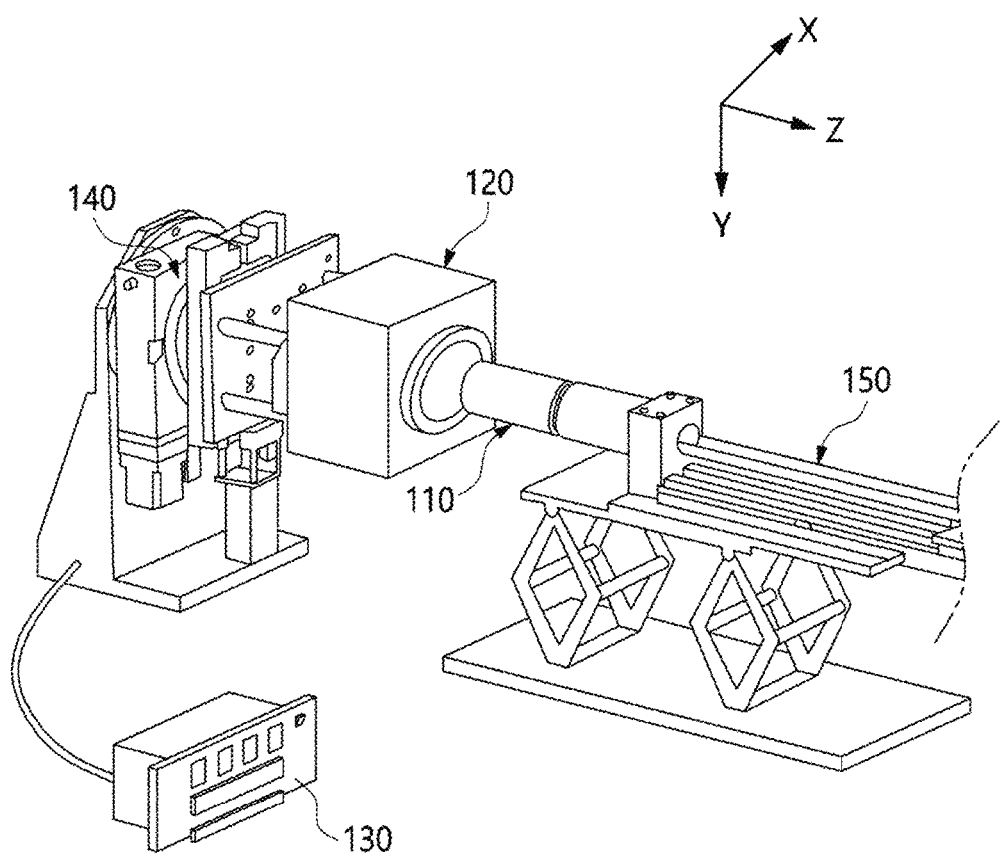
FIG. 2 is an exemplary view illustrating the structure of an apparatus for imaging nano magnetic particles according to an embodiment.

FIG. 1 is a schematic block diagram of an apparatus for imaging nano magnetic particles according to an embodiment, and FIG. 2 is an exemplary view illustrating the structure of an apparatus for imaging nano magnetic particles according to an embodiment.

Referring to FIG. 1, the nano-magnetic-particle-imaging apparatus 1 according to an embodiment may include a measurement head 110, a field-free region generation unit 120, a control unit 130, a first driving unit 140, and a second driving unit 150.

In the measurement head 110, a through hole in which a sample including nano magnetic particles is accommodated is formed, and an excitation coil 111 and a detection coil 112 are installed. Here, the excitation coil 111 generates a magnetic field in the measurement head 110, into which the sample including nano magnetic particles is inserted. Here, the detection coil 112 may acquire a detection signal from the sample placed in the through hole in the measurement head 110.

The field-free region generation unit 120 forms a field-free region, in which there is a weak magnetic field or no magnetic field, inside a spacing area between identical magnetic poles that face each other.

Here, the basic principle of signal acquisition in Magnetic Particle Imaging (MPI) is based on a harmonic signal caused by nonlinear magnetic properties of Nano Magnetic Particles (NMP) in a gradient magnetic field. Here, two identical magnetic poles are made to face each other, which causes saturation without generation of a nonlinear magnetization phenomenon, whereby a field-free region is generated in a predetermined area of the spacing area. Additionally, the field-free region is moved in the space, and imaging is realized using the spatial location at which a harmonic signal is generated.

Here, the field-free region may be a Field-Free Point (FFP) or a Field-Free Line (FFL).

According to an embodiment, the field-free region generation unit 120 includes a pair of rectangular-shaped magnets and a pair of magnet arrays, in each of which multiple small magnets are arranged, thereby forming an FFL having a high magnetic gradient.

That is, as described above, an embodiment is configured to generate an FFL based on a permanent magnet but to replace the permanent magnet with a Halbach array in order to overcome problems of high power consumption and complexity of equipment design, which are characteristics of a conventional magnetic imaging system. Here, the Halbach array is arrangement of multiple small magnets in a predetermined array form, and enables the strength and direction of a magnetic field to be adjusted.

The control unit 130 controls the overall process of nano magnetic particle imaging by controlling the components. Here, the control unit 130 may include any of all types of devices capable of processing data, such as a processor. Here, the term 'processor' may indicate, for example, a data-processing device embedded in hardware, which has a physically structured circuit in order to perform a function expressed using code or instructions included in a program.

According to an embodiment, when the measurement head 110 is located in the through-hole area of the field-free region generation unit 120, the control unit 130 may apply a signal to the excitation coil 111, perform control so as to move the field-free region within a sample, and image the 3D positional distribution of the nano magnetic particles included in the sample based on a detection signal output from the detection coil 112. According to an embodiment, the control unit 130 performs control so as to continuously move the FFP or FFL, and arranges and shows the detection signals, which are detected when the sample overlaps the FFP or FFL, thereby acquiring 3D image information corresponding to the nano magnetic particles. For example, the 3D image information may include stereoscopic image information in the form of a contour plot.

Here, the control unit 130 may generate a 2D image, which is the 2D positional distribution of the nano magnetic particles included in the cross section of the sample, based on the detection signal, and may generate a 3D image by synthesizing multiple 2D images corresponding to multiple cross sections that are parallel to each other. Here, the cross section of the sample may, for example, be parallel to the XY plane illustrated in FIG. 2.

Here, the control unit 130 linearly moves the field-free region in one direction from the cross section of the sample and then linearly moves the field-free region in another direction, which forms a predetermined unit angle with the one direction. Then, the control unit 130 generates a sinogram using a signal that is output from the detection signal according to the movement of the field-free region and performs inverse radon transformation on the generated sinogram, thereby generating a 2D image.

Here, the sinogram corresponds to projection data that is acquired from one direction and is then sequentially arranged in the projection direction. In the sinogram, the pixel values in each row match the amplitude of the corresponding profile at the corresponding position. The sinogram is well-known art, and thus a detailed description thereof will be omitted. Also, the inverse radon transform is a 2D image generation method using a sinogram, which is widely used for CT or the like. Inverse radon transform is technology published in the paper written by Kak, A. C., and M. Slaney and titled "Principles of Computerized Tomographic Imaging" (New York, N.Y., IEEE press, 1988), so a detailed description thereof will be omitted.

For example, referring to FIG. 2, the field-free region may be rotated by the predetermined unit angle from the XY plane, or may be linearly moved in the state in which the field-free region is rotated. This may be referred to as T-round stage movement.

Accordingly, the nano-magnetic-particle-imaging apparatus 1 according to an embodiment may include the first driving unit 140 for rotating or linearly moving the field-free region generation unit 120.

Also, the control unit 130 may repeat the generation of a 2D image while moving the measurement head 110 by a predetermined unit length in a direction perpendicular to the cross section of the sample. That is, when the measurement head 110 is linearly moved in the Z-axis direction, 2D images for the respective cross sections through which the field-free region passes may be acquired.

To this end, the nano-magnetic-particle-imaging apparatus 1 according to an embodiment may include the second driving unit 150 for moving the measurement head 110 to the spacing area of the field-free region generation unit 120.

Hereinbelow, the field-free region generation unit 120 according to an embodiment will be described in detail.

Figure 3:
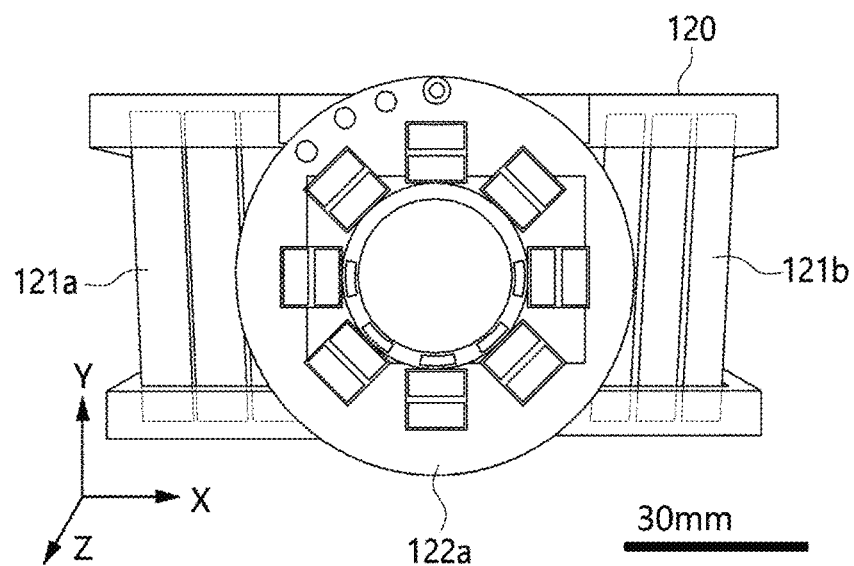
FIG. 3 is an exemplary view illustrating one surface of the housing of a field-free region generation unit according to an embodiment.
Figure 4:
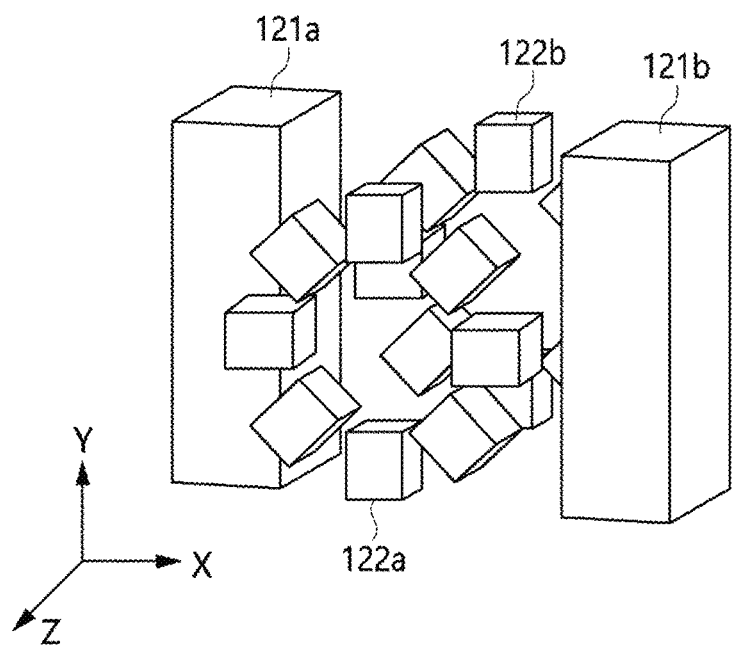
FIG. 4 is a view illustrating the arrangement of rectangular-shaped magnets and an array of small magnets in a field-free region generation unit according to an embodiment.
Figure 5:
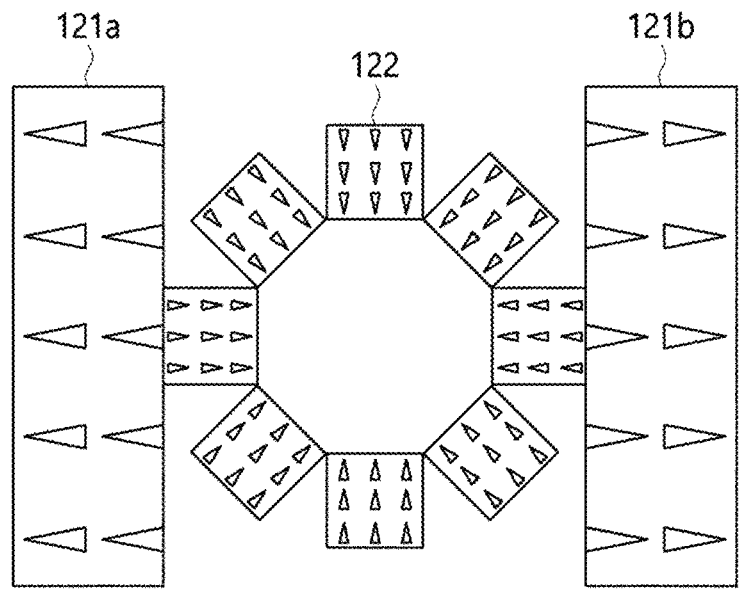
FIG. 5 is an exemplary view illustrating the directions of magnetic fields depending on the arrangement of rectangular-shaped magnets and an array of small magnets in a field-free region generation unit according to an embodiment.
Figure 6:
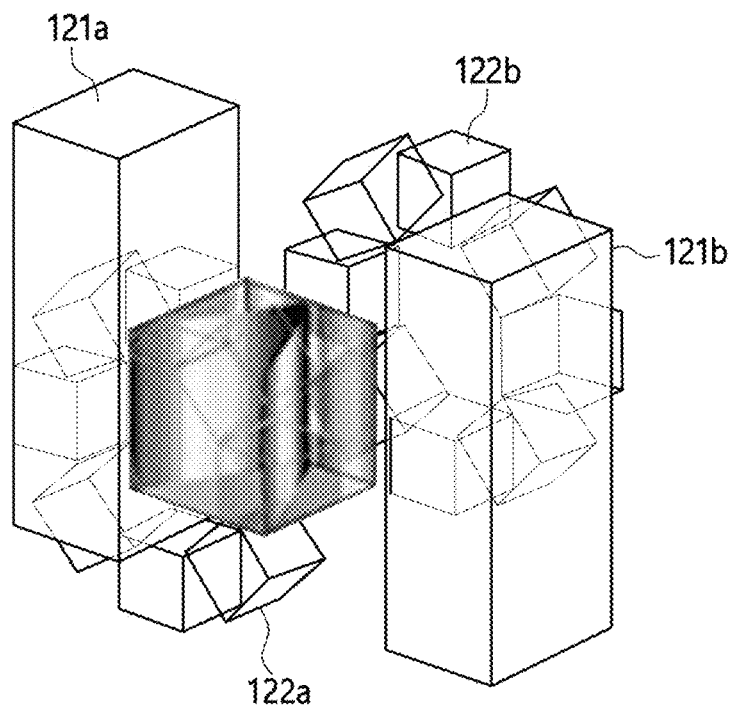
FIG. 6 is an exemplary view illustrating the generation of a field-free region depending on the arrangement of rectangular-shaped magnets and an array of small magnets in a field-free region generation unit according to an embodiment.

FIG. 3 is an exemplary view illustrating one surface of the housing of a field-free region generation unit according to an embodiment, FIG. 4 is a view illustrating the arrangement of rectangular-shaped magnets and an array of small magnets in a field-free region generation unit according to an embodiment, FIG. 5 is an exemplary view illustrating the directions of magnetic fields depending on the arrangement of rectangular-shaped magnets and an array of small magnets in a field-free region generation unit according to an embodiment, and FIG. 6 is an exemplary view illustrating the generation of a field-free region depending on the arrangement of rectangular-shaped magnets and an array of small magnets in a field-free region generation unit according to an embodiment.

Referring to FIG. 3, the field-free region generation unit 120 includes a hexahedral housing having an opening formed in a first surface thereof such that a measurement head is inserted into a spacing area.

In the housing, a pair of rectangular-shaped magnets 121*a* and 121*b* may be installed respectively on two surfaces facing each other, among four surfaces perpendicular to the first surface, and a pair of magnet arrays 122*a*, in each of which multiple small magnets are arranged along the edge of the opening, may be installed respectively on the first surface of the housing and on another surface facing the first surface.

According to an embodiment, the multiple small magnets 122*a* or 122*b* may be arranged along the edge of the opening in the shape of a ring, as illustrated in FIG. 4. Accordingly, a path via which a sample for imaging nano magnetic particles can be inserted into the field-free region may be formed.

Here, the pair of rectangular-shaped magnets 121*a* and 121*b* and the pair of arrays of small magnets 122*a* and 122*b* may be NEODIUM magnets (n 30 grade). However, this is merely an example, and the present invention is not limited thereto. That is, magnets having stronger magnetism may be used for the small magnets, and, in proportion to the strength of magnetism, a field-free region having a sharper gradient may be acquired.

Here, the pair of rectangular-shaped magnets 121*a* and 121*b* and the pair of arrays of small magnets 122*a* and 122*b* may form a magnetic field, as illustrated in FIG. 5. Here, the magnetization direction of the pair of arrays of small magnets 122*a* and 122*b* may be expressed as 'k=0'.

Also, depending on the magnetic field formed by the pair of rectangular-shaped magnets 121*a* and 121*b* and the pair of arrays of small magnets 122*a* and 122*b*, a field-free region resembling the simulation image illustrated in FIG. 6 may be generated.

As described above, a field-free region may be formed in the center of the space surrounded by the pair of rectangular-shaped magnets 121*a* and 121*b* and the pair of arrays of small magnets 122*a* and 122*b*.

Also, according to an embodiment, the pair of arrays of small magnets 122*a* and 122*b* may be fixed, and the first driving unit 140 may linearly move the pair of rectangular-shaped magnets 121*a* and 121*b* in one direction, or may rotate the same so as to form a predetermined angle θ with the one direction. That is, the pair of rectangular-shaped magnets 121*a* and 121*b* is repeatedly moved to the left or right in the XY plane, or is repeatedly rotated by θ degrees in the XY plane until it has been rotated by 180 degrees, whereby the field-free region for MPI imaging may be moved to the left or right or rotated by θ degrees until it has been rotated by 180 degrees.

Figure 7:
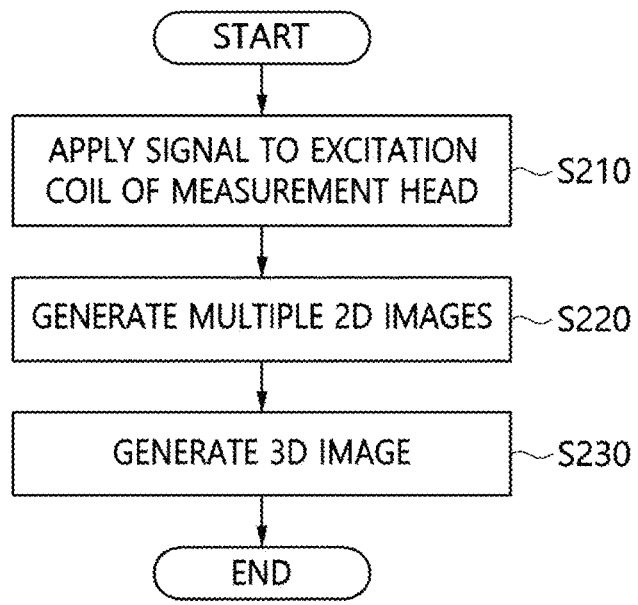
FIG. 7 is a flowchart for explaining a method for imaging nano magnetic particles according to an embodiment.

FIG. 7 is a flowchart for explaining a method for imaging nano magnetic particles according to an embodiment.

Referring to FIG. 7, the method for imaging nano magnetic particles according to an embodiment may include applying a signal to an excitation coil installed in a measurement head that accommodates a sample including nano magnetic particles at step S210 and imaging the 3D positional distribution of the nano magnetic particles included in the sample based on a detection signal that is output from the detection coil of the measurement head by moving a magnetic-field-free region, which is generated in a spacing area between the identical magnetic poles facing each other, in the sample at steps S220 to S230.

Here, imaging the 3D positional distribution of the nano magnetic particles may include generating a 2D image, which is the 2D positional distribution of the nano magnetic particles included in the cross section of the sample, based on the detection signal at step S220 and generating a 3D image by synthesizing multiple 2D images corresponding to multiple cross sections that are parallel to each other at step S230.

Here, generating the 2D image at step S220 may be configured such that, while a pair of rectangular-shaped magnets is linearly moved in one direction (c.f., FIGS. 8 to 12) or is rotated so as to form a predetermined angle with the one direction (c.f., FIGS. 13 to 22), a sinogram is generated using a signal output from the detection signal according to the movement of the field-free region, and a 2D image is generated by performing inverse radon transform on the generated sinogram.

FIGS. 8 to 12 are views illustrating the movement of a field-free line according to the movement of a pair of rectangular-shaped magnets in one direction according to an embodiment.

Figure 8:
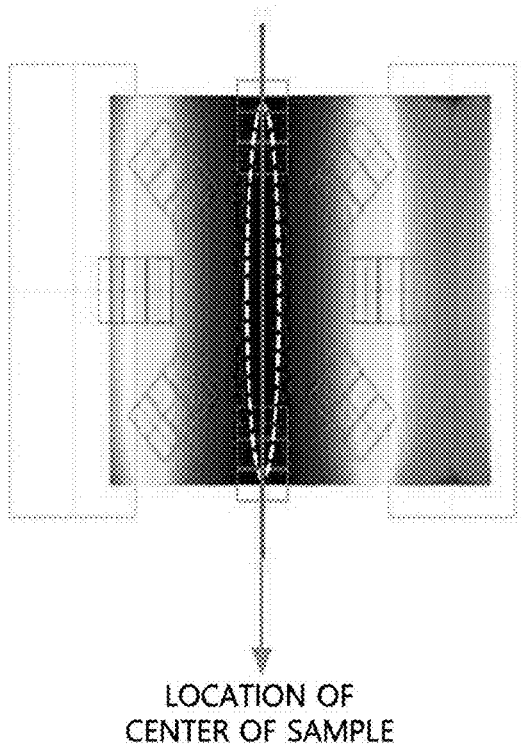
FIGS. 8 to 12 are views illustrating the movement of a field-free line when a pair of rectangular-shaped magnets moves in a direction according to an embodiment.
Figure 9:
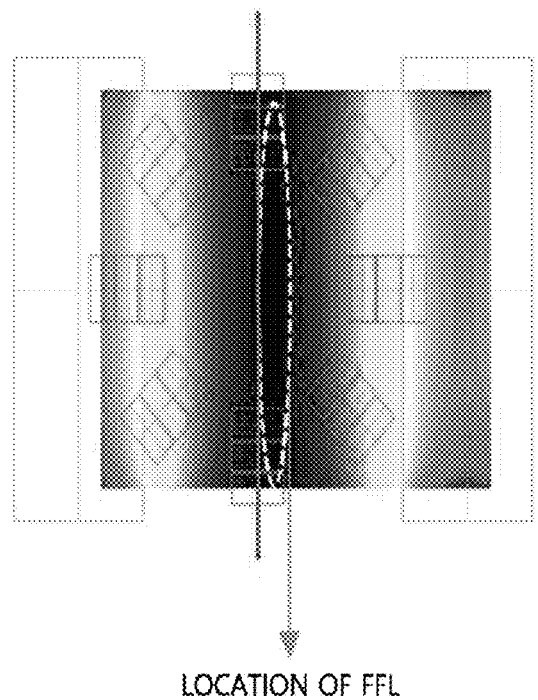
Figure 10:
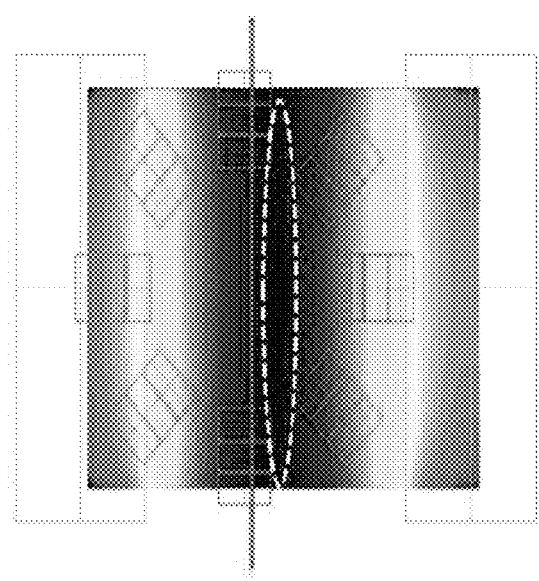
Figure 11:
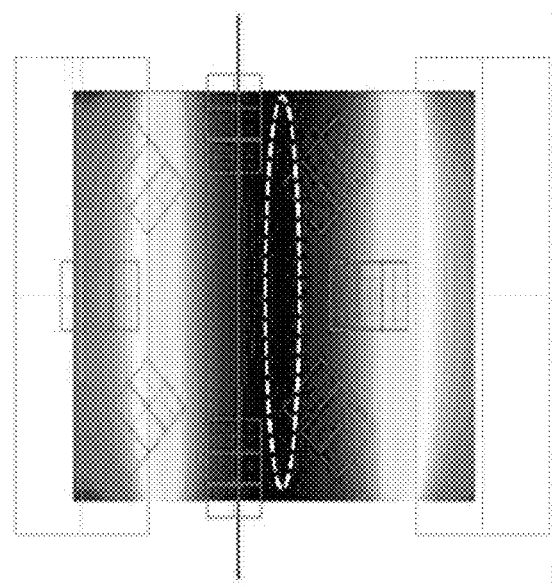
Figure 12:
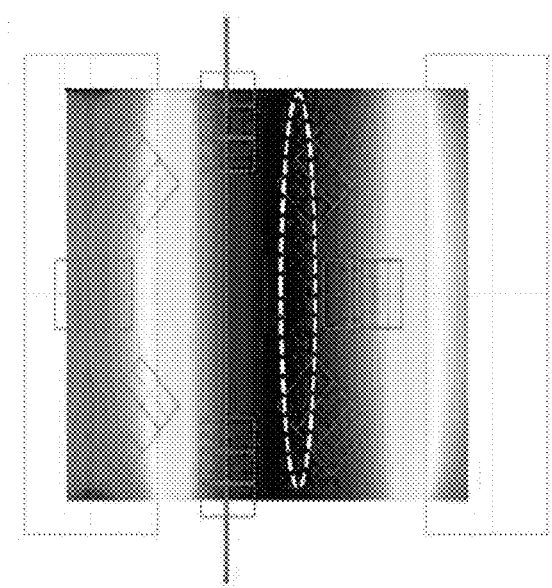

Referring to FIG. 8, in the state in which the field-free line is located at the center of a sample, when a pair of rectangular-shaped magnets 121*a* and 121*b* moves to the right, the field-free line also moves to the right gradually, one step at a time, as shown in FIGS. 8 to 12.

FIGS. 13 to 22 are views illustrating the rotation of a field-free line according to the rotation of a pair of rectangular-shaped magnets according to an embodiment.

Figure 13:
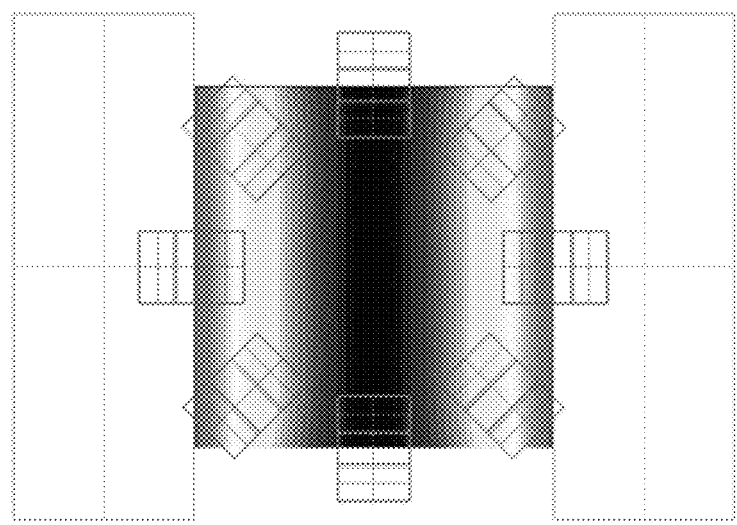
FIGS. 13 to 22 are views illustrating the rotation of a field-free line when a pair of rectangular-shaped magnets rotates according to an embodiment.
Figure 14:
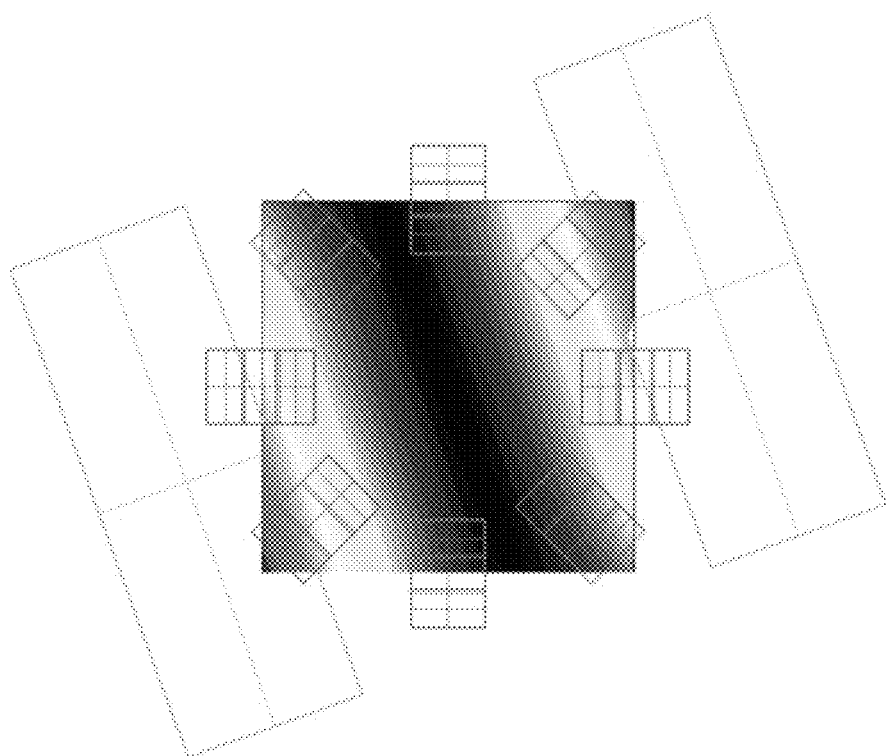
Figure 15:
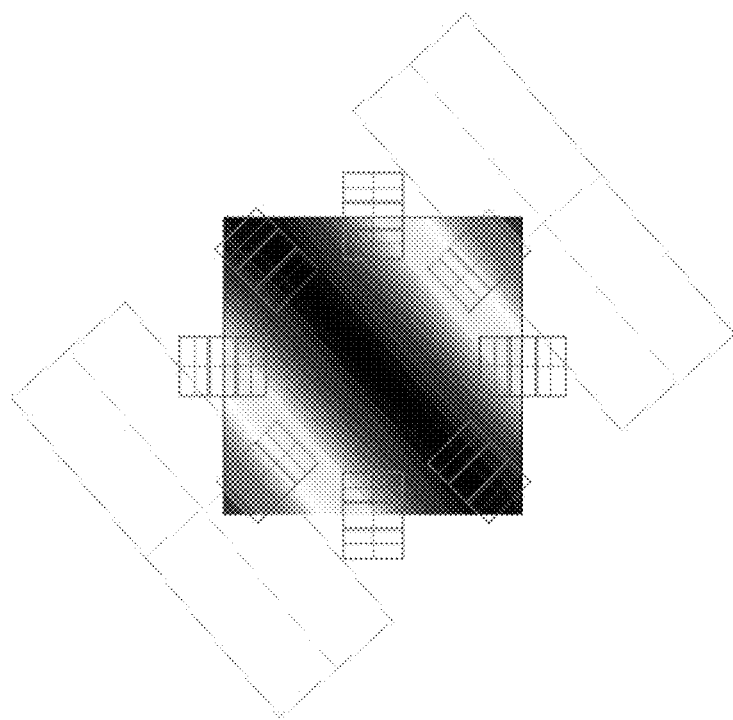
Figure 16:
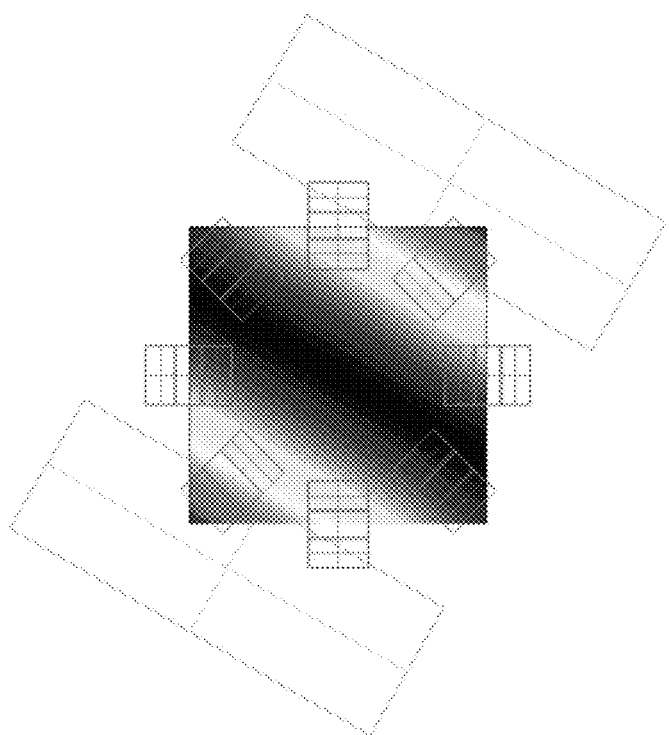
Figure 17:
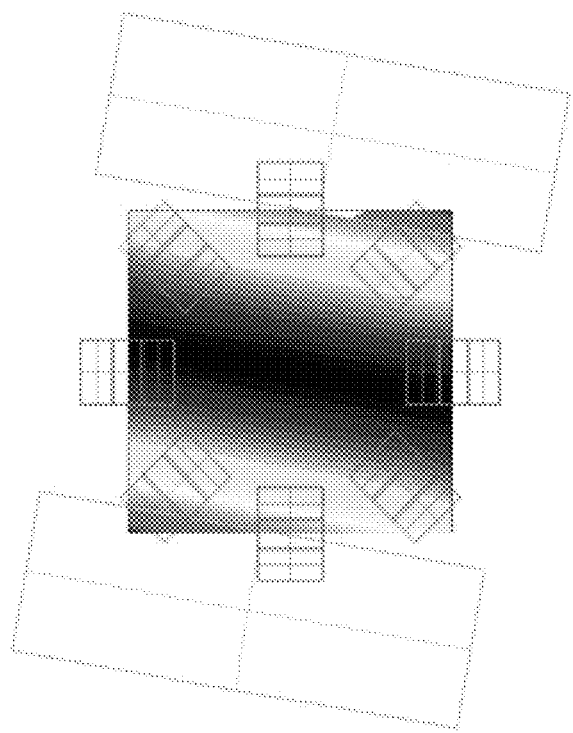
Figure 18:
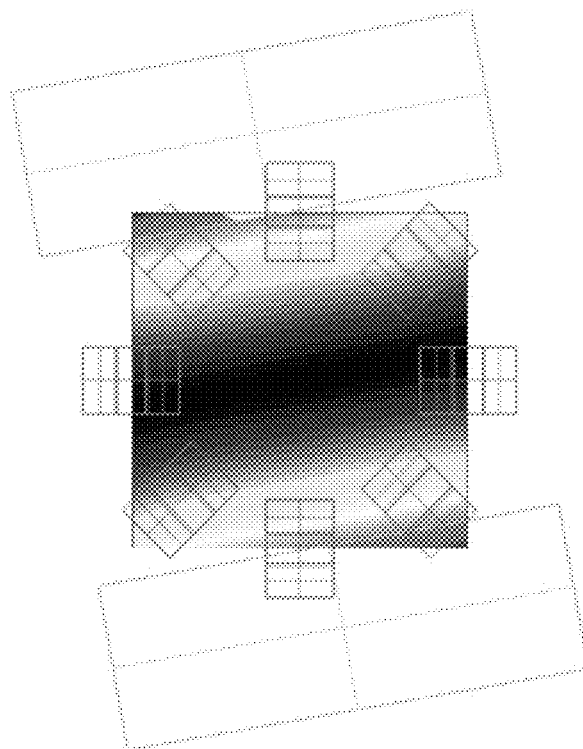
Figure 19:
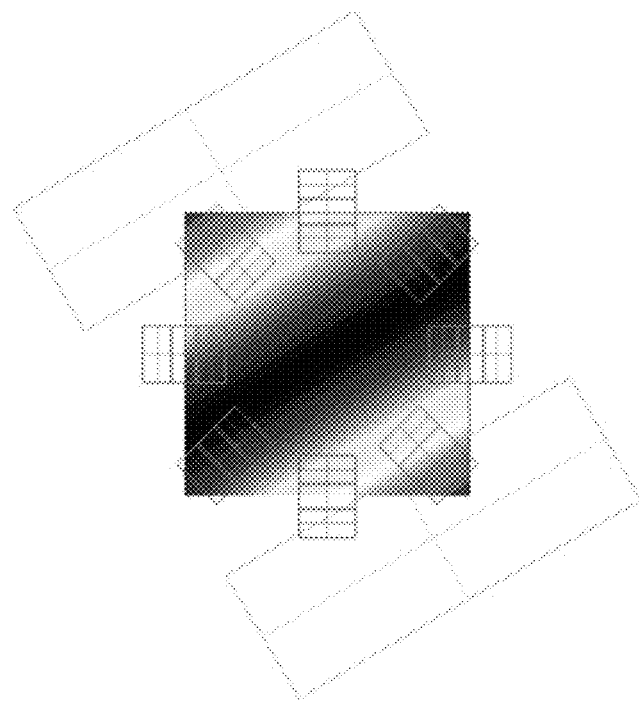
Figure 20:
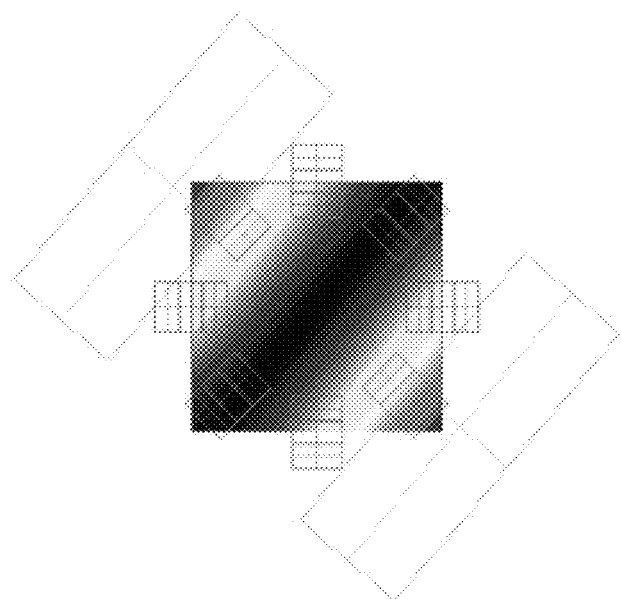
Figure 21:
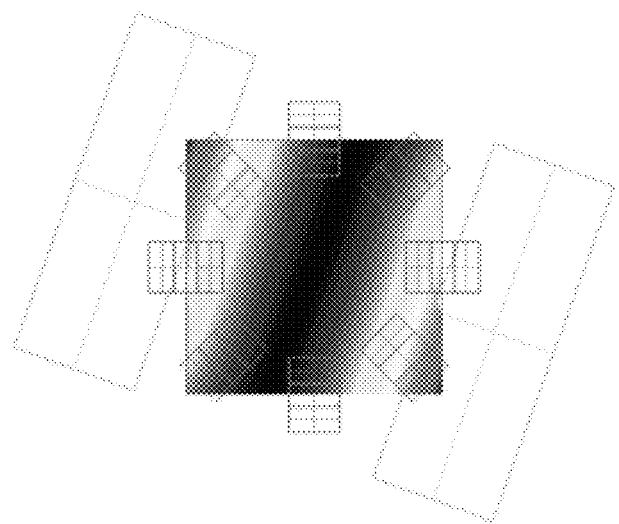
Figure 22:
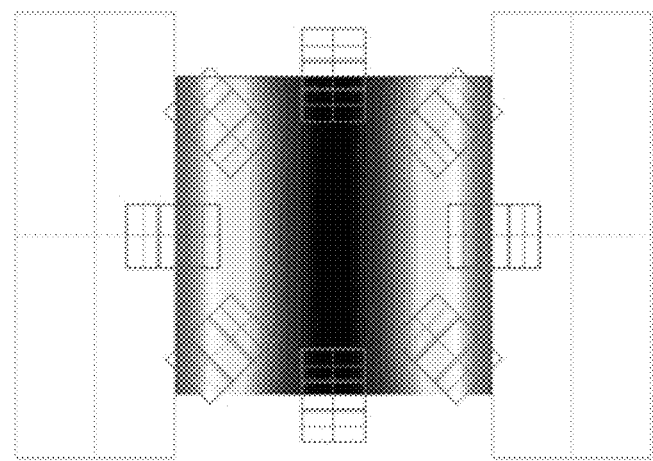

Referring to FIG. 13, in the state in which a field-free line is located at the center of a sample, when a pair of rectangular-shaped magnets 121*a* and 121*b* is repeatedly rotated anticlockwise by θ degrees (e.g., 20 deg), the field-free line is also repeatedly rotated anticlockwise by θ degrees, thereby having being rotated by 180 degrees, as illustrated in FIGS. 13 to 22.

Here, generating the 2D image may be repeated while the measurement head is moved by a predetermined unit length in a direction perpendicular to the cross section of the sample.

The above-described field-free region generation unit 120 according to an embodiment may be used for a small MPI scanner.

Here, when a sample having a diameter equal to or less than 20 mm is measured, a scanner in which the gradient field of an FFL is 10 T/m may be used as a high-resolution scanner having a resolution equal to or less than 1 mm.

FIGS. 23 to 26 are exemplary views illustrating the performance of a small MPI scanner to which a field-free region generation unit according to an embodiment is applied.

Figure 23:
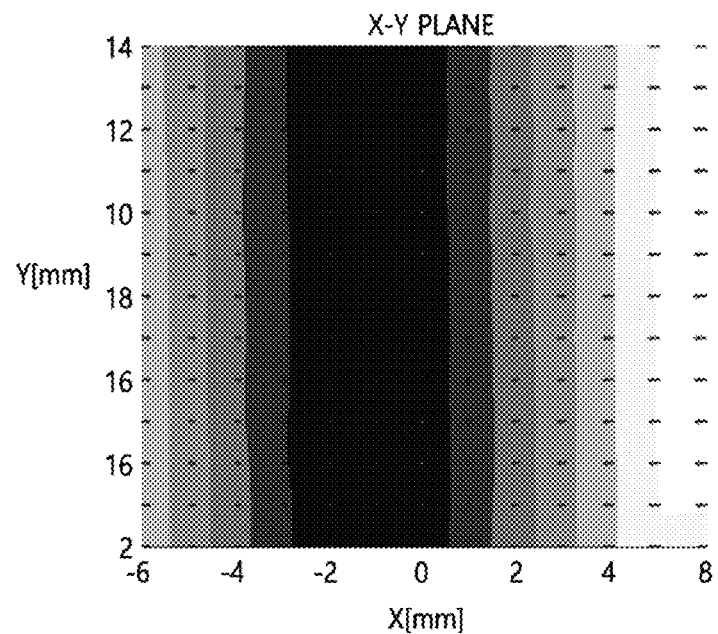
FIGS. 23 to 26 are exemplary views illustrating the performance of a small MPI scanner to which a field-free region generation unit according to an embodiment is applied.
Figure 24:
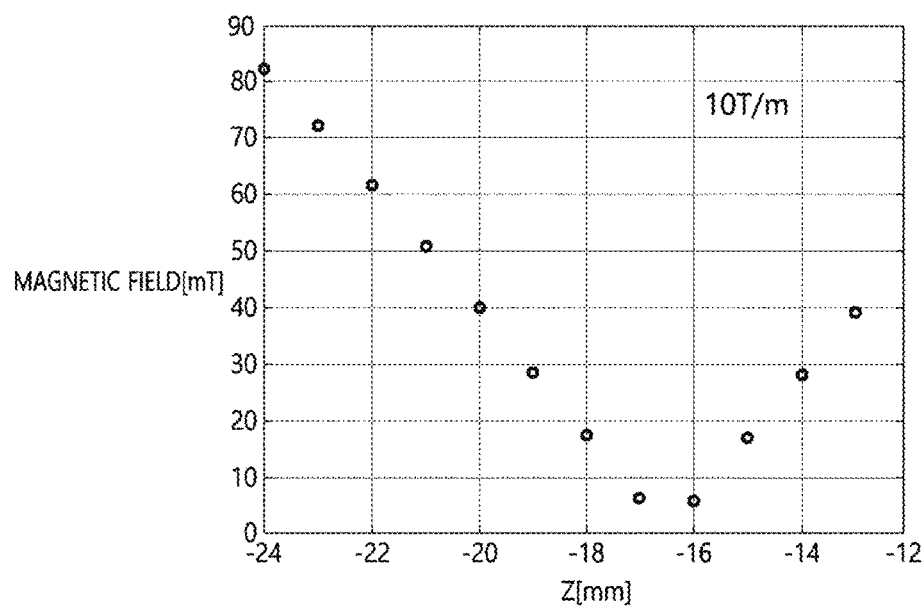
Figure 25:
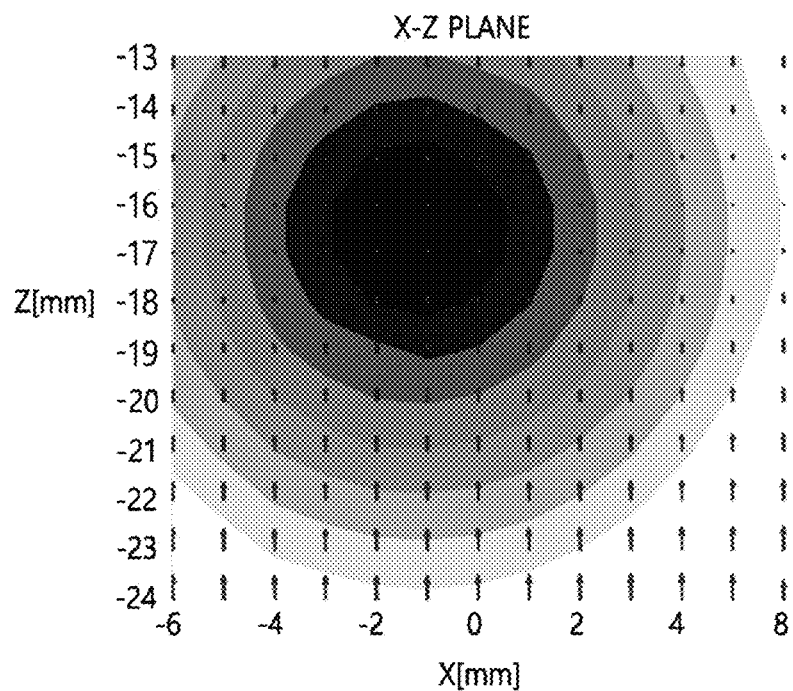
Figure 26:
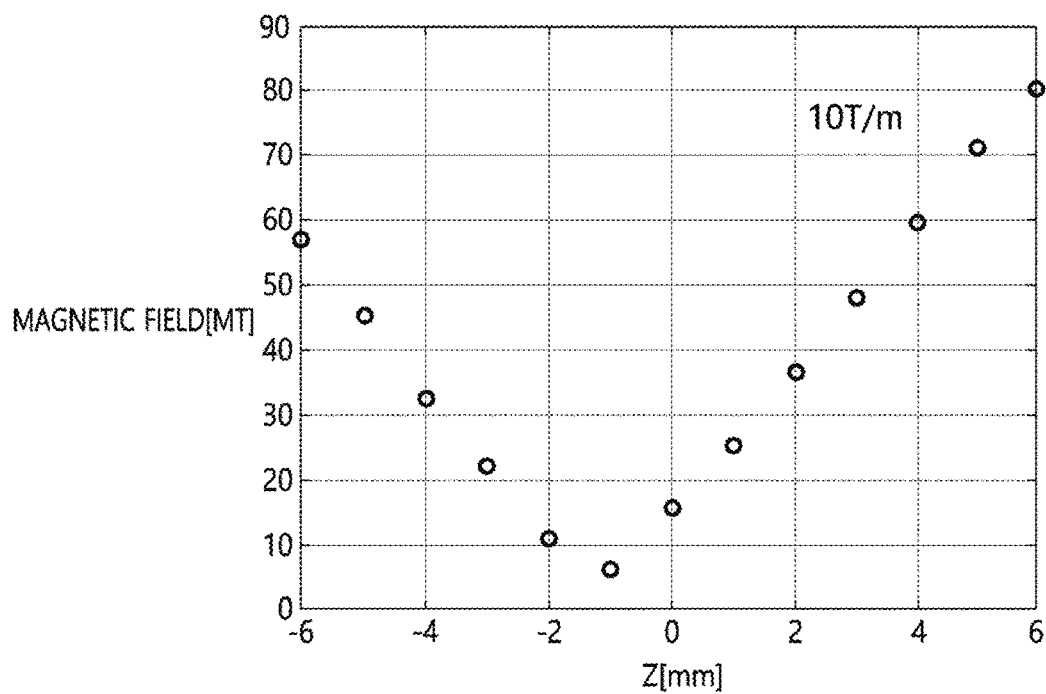
Figure 27:
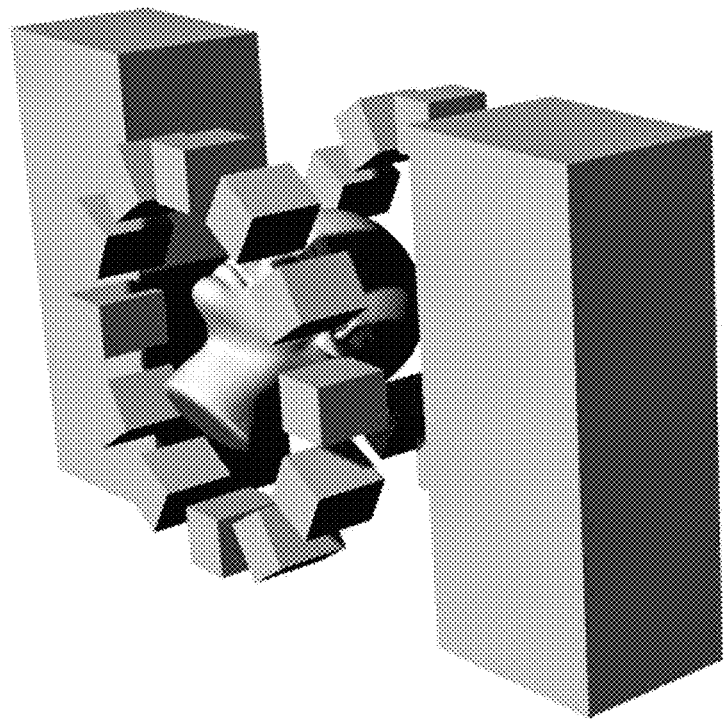
FIGS. 27 to 30 are exemplary views illustrating the structure of an MPI brain scanner to which a field-free region generation unit according to an embodiment is applied.
Figure 28:
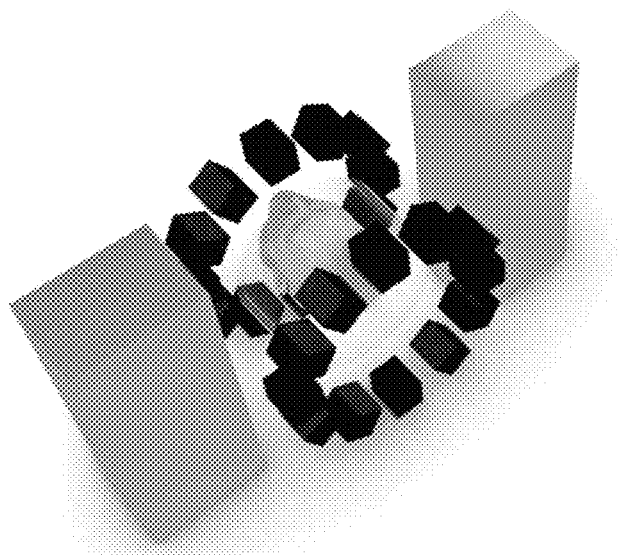
Figure 29:
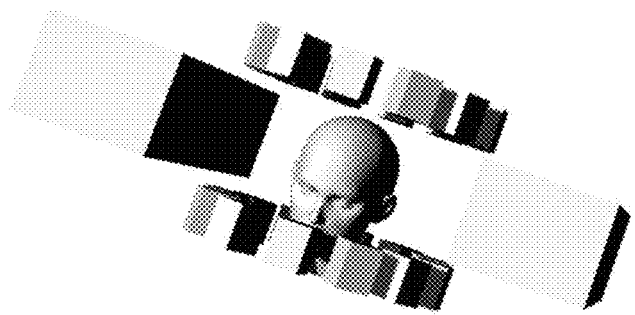
Figure 30:
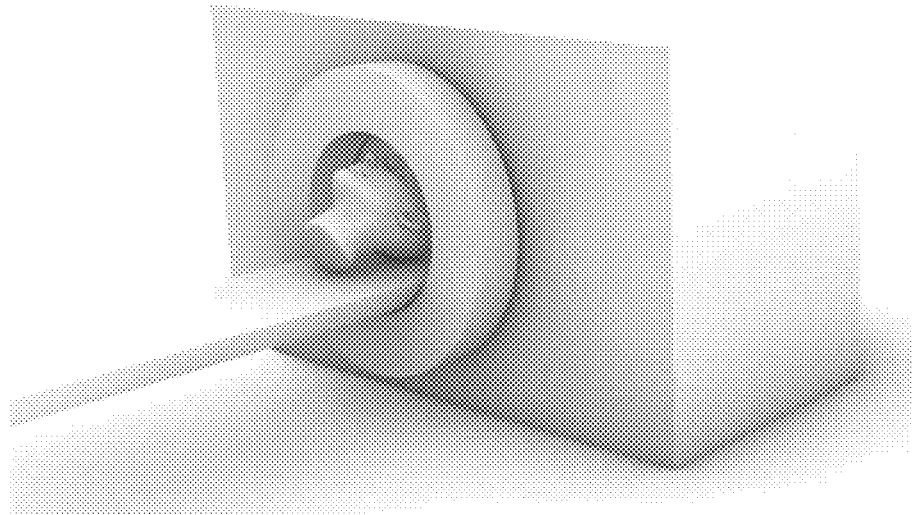

FIG. 23 is a result of measurement of a magnetic field on the X-Y plane, FIG. 24 is a result of measurement of a magnetic gradient (10 T/m) along the Z-axis, FIG. 25 is a result of measurement of a magnetic field on the X-Z plane, and FIG. 26 illustrates a result of measurement of a magnetic gradient (10 T/m) along the Y-axis. That is, an FFL having a magnetic gradient (equal to or greater than 2 T/m) required for clinical research may be realized under real-world conditions according to an embodiment.

Meanwhile, the field-free region generation unit 120 according to an embodiment may facilitate the production of an MPI device capable of scanning the brain of a human or an animal.

FIGS. 27 to 30 are exemplary views illustrating the structure of an MPI brain scanner to which a field-free region generation unit according to an embodiment is applied.

As illustrated in FIGS. 27 to 30, a device capable of scanning the brain of a human or an animal may be developed by making it possible for the brain of a human or an animal to pass the inside of a Halbach array of magnets and by arranging rectangular-shaped magnets suitable therefor on the left and right sides thereof. In this manner, application of another device for scanning other body parts may be realized.

Figure 31:
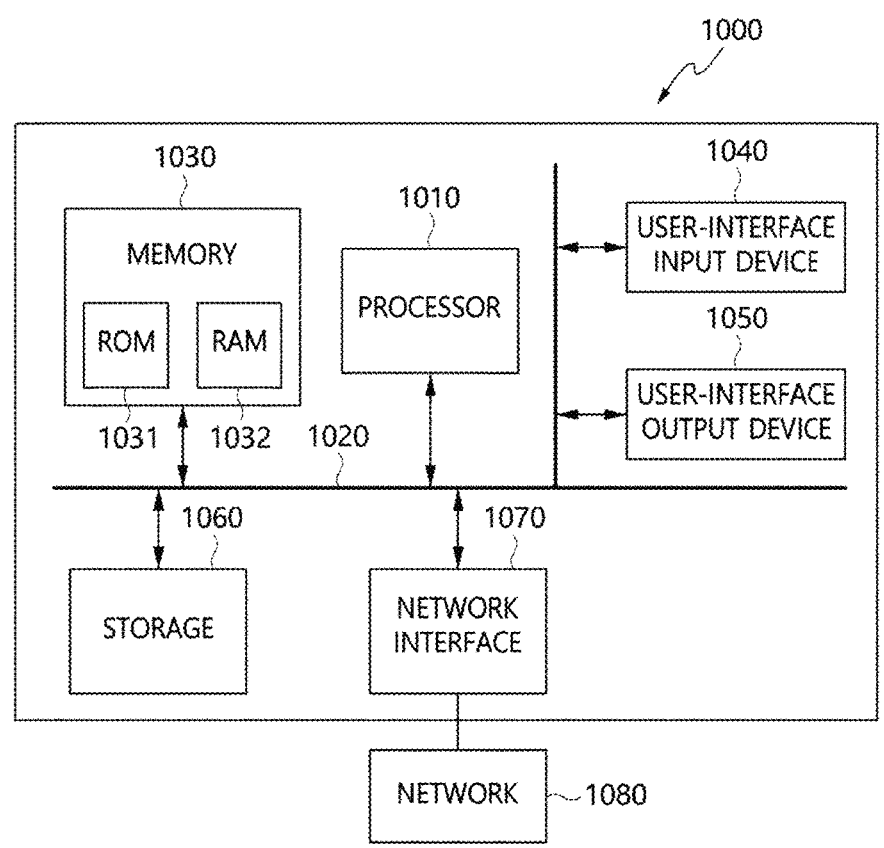
FIG. 31 is a view illustrating a computer system configuration according to an embodiment.

FIG. 31 is a view illustrating a computer system configuration according to an embodiment.

The control unit 130 according to an embodiment may be implemented in a computer system 1000 including a computer-readable recording medium.

The computer system 1000 may include one or more processors 1010, memory 1030, a user-interface input device 1040, a user-interface output device 1050, and storage 1060, which communicate with each other via a bus 1020. Also, the computer system 1000 may further include a network interface 1070 connected with a network 1080. The processor 1010 may be a central processing unit or a semiconductor device for executing a program or processing instructions stored in the memory 1030 or the storage 1060. The memory 1030 and the storage 1060 may be storage media including at least one of a volatile medium, a non-volatile medium, a detachable medium, a non-detachable medium, a communication medium, and an information delivery medium. For example, the memory 1030 may include ROM 1031 or RAM 1032.

According to an embodiment, the use of small magnets increases freedom from the aspect of space configuration, which makes it easier to place a sample in a field-free region. That is, a conventional method uses a pair of large permanent magnets or a pair of coils in order to generate a field-free region. However, when a permanent magnet having a rectangular shape is used, it is difficult to secure an area via which a sample has to be inserted in order to place the sample near a field-free region. The apparatus for generating a field-free region according to an embodiment provides a window having a fixed size in a sample insertion unit, thereby increasing freedom to move a sample.

According to an embodiment, variation in the strength of a magnetic field is reduced because the size of a magnet is reduced. That is, when a large magnet is used in order to generate a field-free region according to the conventional art, it is difficult to obtain a magnet having uniform magnetic field strength. This is because the greater the size of a magnet, the more difficult the production of a magnet having uniform magnetic field strength. The apparatus for generating a field-free region based on a Halbach array, which is configured as an arrangement of small magnets, according to an embodiment makes it easy to obtain a magnet that generates a magnetic field having uniform strength.

According to an embodiment, a sharper magnetic field gradient may be generated in a field-free region using a magnet that is lighter than a magnet having a large size. That is, resolution in MPI technology is proportional to the magnetic field gradient of a field-free region. In order to acquire a field-free region for covering a large Field-of-View (FOV) in MPI, the field-free region has to be generated using a very large magnet or by applying a high current to a coil. When a field-free region generation apparatus based on a Halbach array, which is configured as an arrangement of small magnets, according to an embodiment is used, generation of a satisfactory field-free region for a preclinical study may be realized using a light device.

According to an embodiment, a field-free region may be formed without a high-cost power supply and without needlessly generating heat. That is, when a pair of coils is used in order to generate a field-free region based on a conventional method, very high power is generally required in order to form a magnetic field having strength comparable to a magnetic field that can be generated using a permanent magnet. Accordingly, a high-cost power supply is required, and a significant amount of heat is generated from the coil. When a field-free region is formed using a combination of small magnets according to an embodiment, the expense for supplying power may be reduced, and heat generation may be avoided.

According to an embodiment, high-resolution MPI equipment may be produced to be smaller, lighter, and less expensive using an arrangement of small magnets. That is, when the size of a magnet is greater than 50 mm×50 mm, it is difficult to purchase a commercially available magnet (a magnet that can be purchased directly from a specialized magnet wholesaler or retailer). Accordingly, it is necessary to request a magnet manufacturer to produce the same, which increases expenses several to hundreds of times compared to when a commercially available magnet is used.

Although embodiments of the present invention have been described with reference to the accompanying drawings, those skilled in the art will appreciate that the present invention may be practiced in other specific forms without changing the technical spirit or essential features of the present invention. Therefore, the embodiments described above are illustrative in all aspects and should not be understood as limiting the present invention.

What is claimed is:

1. An apparatus for generating a field-free region, comprising:

a hexahedral housing in which an opening, into which a measurement head is inserted, is formed in a first surface thereof;

a pair of rectangular-shaped magnets that are installed respectively on two surfaces facing each other, among four surfaces perpendicular to the first surface of the housing; and a pair of magnet arrays that are installed respectively on the first surface of the housing and on another surface facing the first surface, each of the magnet arrays including multiple small magnets arranged along an edge of the opening, wherein the measurement head in which a through hole for accommodating a sample is inserted in the direction perpendicular to the first surface.

2. The apparatus of claim 1,
wherein the multiple small magnets are arranged in a circular shape along the edge of the opening.

3. The apparatus of claim 1,
wherein the field-free region is a Field-Free Point (FFP) or a Field-Free Line (FFL).

4. The apparatus of claim 1, further comprising:
a first driving unit for linearly moving or rotating the pair of rectangular-shaped magnets.

5. An apparatus for imaging nano magnetic particles, comprising:
a measurement head in which a through hole for accommodating a sample including the nano magnetic particles is formed and in which an excitation coil and a detection coil are installed;

a field-free region generation unit for forming a field-free region, in which there is a weak magnetic field or no magnetic field, in a spacing area between identical magnetic poles that face each other; and a control unit for applying a signal to the excitation coil when the measurement head is placed within the spacing area of the field-free region generation unit, controlling the field-free region so as to move in the sample, and imaging 3D positional distribution of the nano magnetic particles included in the sample based on a detection signal output from the detection coil, wherein the field-free region generation unit includes a pair of rectangular-shaped magnets and a pair of magnet arrays, in each of which multiple small magnets are arranged, wherein the field-free region generation unit includes:
a hexahedral housing in which an opening, into which a measurement head is inserted, is formed in a first surface thereof, the pair of rectangular-shaped magnets that are installed respectively on two surfaces facing each other, among four surfaces perpendicular to the first surface of the housing, and the pair of magnet arrays that are installed respectively on the first surface of the housing and on another surface facing the first surface, each of the magnet arrays including the multiple small magnets arranged along an edge of the opening, wherein the measurement head is inserted in the direction perpendicular to the first surface.

6. The apparatus of claim 5,
wherein the multiple small magnets are arranged in a circular shape along the edge of the opening.

7. The apparatus of claim 5,
wherein the field-free region is a Field-Free Point (FFP) or a Field-Free Line (FFL).

8. The apparatus of claim 5, wherein the control unit is configured to:
generate a 2D image, which is 2D positional distribution of nano magnetic particles included in a cross section of the sample, based on the detection signal; and generate a 3D image by synthesizing multiple 2D images corresponding to multiple cross sections that are parallel to each other.

9. The apparatus of claim 8, further comprising:
a first driving unit for linearly moving or rotating the pair of rectangular-shaped magnets.

10. The apparatus of claim 9, wherein the control unit is configured to:
repeatedly perform linear movement of the pair of rectangular-shaped magnets in one direction and rotation thereof so as to form a predetermined angle with the one direction by controlling the first driving unit, and generate a sinogram using a signal output from the detection signal according to movement of the field-free region and generate the 2D image by performing inverse radon transform on the generated sinogram.

11. The apparatus of claim 10, further comprising:
a second driving unit for moving the measurement head to the spacing area via the opening in the field-free region generation unit.

12. The apparatus of claim 11,
wherein the control unit repeats generation of the 2D image while moving the measurement head by a predetermined unit length in a direction perpendicular to the cross section of the sample.

13. A method performed by an apparatus for imaging nano magnetic particles, the apparatus including a processor and a memory operably coupled to the processor, wherein the memory stores program instructions to be executed by the processor, the method comprising:
applying, performed by the processor, a signal to an excitation coil installed in a measurement head that accommodates a sample including the nano magnetic particles; and moving, performed by the processor, a field-free region, in which there is a weak magnetic field or no magnetic field and which is generated in a spacing area between identical magnetic poles facing each other, in a sample;

detecting, performed by the processor, a signal output from a detection coil of the measurement head; and transforming, performed by the processor, a detection signal into a 3D image which is 3D positional distribution of the nano magnetic particles included in the sample, wherein the field-free region is generated by a pair of rectangular-shaped magnets and a pair of magnet arrays, in each of which multiple small magnets are arranged, wherein the pair of rectangular-shaped magnets is configured such that the rectangular-shaped magnets are installed respectively on two surfaces facing each other, among four surfaces perpendicular to a first surface of a hexahedral housing, in the first surface of which an opening, into which a measurement head is inserted, is formed in a first surface, wherein the pair of magnet arrays is configured such that the magnet arrays are located respectively on the first surface of the housing and on another surface facing the first surface and such that the multiple small magnets are arranged along an edge of the opening, and wherein the measurement head is inserted in the direction perpendicular to the first surface.

14. The method of claim 10,
wherein the multiple small magnets are arranged in a circular shape along the edge of the opening.

15. The method of claim 10,
wherein the field-free region is a Field-Free Point (FFP) or a Field-Free Line (FFL).

16. The method of claim 10, wherein transforming the detection signal into the 3D image comprises:
generating a 2D image, which is 2D positional distribution of nano magnetic particles included in a cross section of the sample, based on the detection signal; and
generating a 3D image by synthesizing multiple 2D images corresponding to multiple cross sections that are parallel to each other.

17. The method of claim 16, wherein generating the 2D image comprises;
generating a sinogram using a signal output from the detection signal according to movement of the field-free region while the pair of rectangular-shaped magnets is linearly moved in one direction or is rotated so as to form a predetermined angle with the one direction; and
generating the 2D image by performing inverse radon transform on the generated sinogram.

18. The method of claim 17,
wherein generating the 2D image is repeated while moving the measurement head by a predetermined unit length in a direction perpendicular to the cross section of the sample.

\* \* \* \* \*

UNITED STATES PATENT AND TRADEMARK OFFICE
CERTIFICATE OF CORRECTION

PATENT NO. : 11,707,202 B2
APPLICATION NO. : 17/466898
DATED : July 25, 2023
INVENTOR(S) : Jin-Sun Kim, Jae-Chan Jong and Hyo-Bong Hong It is certified that error appears in the above-identified patent and that said Letters Patent is hereby corrected as shown below:

In the Claims

Column 13, Line 1:
Please replace: "14. The method of claim 10,
wherein the multiple small magnets are arranged in a circular shape along the edge of the opening."
With --14. The method of claim 13,
wherein the multiple small magnets are arranged in a circular shape along the edge of the opening.--

Column 13, Line 4:
Please replace: "15. The method of claim 10,
wherein the field-free region is a Field-Free Point (FFP) or a Field-Free Line (FFL)."
With --15. The method of claim 13,
wherein the field-free region is a Field-Free Point (FFP) or a Field-Free Line (FFL).--

Signed and Sealed this
Nineteenth Day of September, 2023

Katherine Kelly Vidal
*Director of the United States Patent and Trademark Office*